Figure 1:
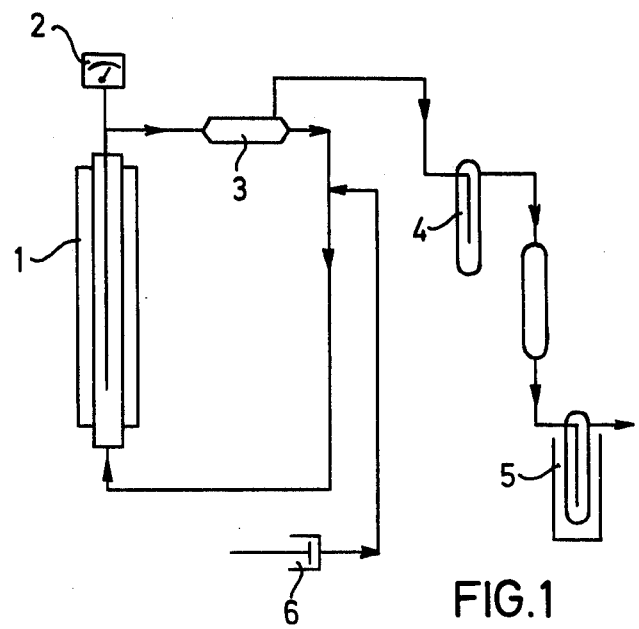
Figure 2:
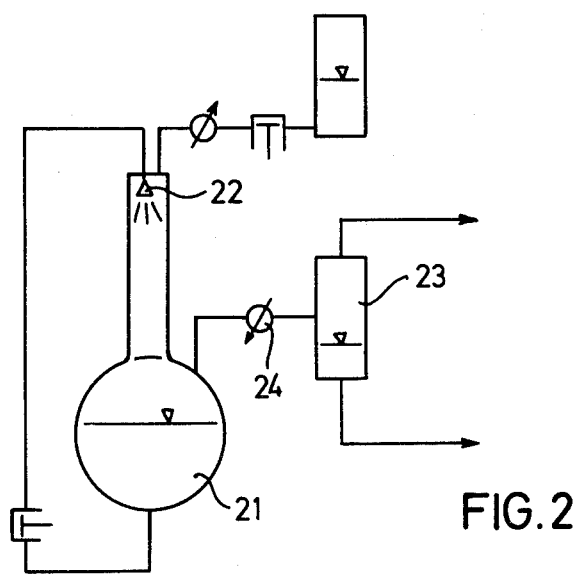

United States Patent [19]

Weitz et al.

[11] 4,158,008
[45] Jun. 12, 1979

[54] MANUFACTURE OF PROPYLENE OXIDE

[75] Inventors: Hans-Martin Weitz, Bad Durkheim; Juergen Hartig, Ludwigshafen; Rolf Platz, Mannheim, all of Fed. Rep. of Germany

[73] Assignee: BASF Aktiengesellschaft, Fed. Rep. of Germany

[21] Appl. No.: 879,514

[22] Filed: Feb. 21, 1978

[30] Foreign Application Priority Data

Feb. 23, 1977 [DE] Fed. Rep. of Germany ....... 2707638

[51] Int. Cl.² ........................................... C07D 301/02
[52] U.S. Cl. .............................................. 260/348.16
[58] Field of Search ................................... 260/348.16

[56] References Cited

U.S. PATENT DOCUMENTS

Re. 29,597 3/1978 Brownstein et al. ............ 260/348.16

FOREIGN PATENT DOCUMENTS 2504981 8/1976 Fed. Rep. of Germany ...... 260/348.16

Primary Examiner—Norma S. Milestone
Attorney, Agent, or Firm—Keil & Witherspoon

[57] ABSTRACT

Propylene oxide is prepared by elimination of acetic acid from propylene glycol monoacetates in the presence of a base. In contrast to the conventional elimination of acetic acid in the gas phase, the present reaction is carried out in the liquid phase in a high-boiling solvent. Because of the smaller reaction space required, the reaction in the liquid phase is simpler.

6 Claims, 2 Drawing Figures

MANUFACTURE OF PROPYLENE OXIDE

The present invention relates to a process for the manufacture of propylene oxide by eliminating low molecular weight carboxylic acids from esters of propylene glycol in homogeneous solution at an elevated temperature in the presence of a base.

German Laid-Open Application DOS No. 2,412,136 discloses that alkylene oxides may advantageously be manufactured by catalytic deacyloxylation of vicinal hydroxy-ester compounds in the vapor phase over a solid basic compound. This process gives high yields. However, it suffers from the disadvantage that as a result of the elimination of the acid in the vapor phase, and especially when working under reduced pressure, very large reaction spaces become necessary, entailing high investment costs, for carrying out the reaction.

It is an object of the present invention to carry out this reaction with higher space-time yields.

A higher conversion, based on the reaction space employed, is as a rule achieved with reactions which take place in the liquid phase. However, this inherently obvious measure has hitherto not proved successful, so that there is no recent publication on this subject. U.S. Pat. No. 3,453,189 only discloses that on treating 2-hydroxy-1-acetoxypropane with 10% strength aqueous sodium hydroxide solution a good yield of propylene oxide is obtained. However, this method is economically not viable, since it entails the consumption of stoichiometric amounts of sodium hydroxide solution for the elimination of the acetic acid, whilst the manufacture of 2-hydroxy-1-acetoxypropane by acetoxylation of propylene requires recycling the eliminated acetic acid. Liberating the acetic acid from a sodium acetate solution and recycling it would however be very expensive.

It is an object of the present invention to provide a process, which takes place catalytically in the liquid phase, for decarboxylating alkylene glycol esters, which process does not suffer from the above disadvantages.

We have found, surprisingly, that this object is achieved and that the elimination of carboxylic acid from esters of 1,2-propylene glycol in the presence of bases takes place smoothly in the liquid phase if a homogeneously dissolved monoester of 1,2-propylene glycol and a low molecular weight carboxylic acid, e.g. 1 to 5 carbon atoms, or a corresponding diester which can be converted to the monoester by hydrolysis under the reaction conditions, is heated briefly at from 160° to 380° C. in an organic solvent which boils above the chosen reaction temperature, in the presence of a dissolved base or a basic-reacting salt of such a base, e.g. a salt of such a base with a weak inorganic acid or with a low molecular weight carboxylic acid, and propylene oxide is isolated from the vapor leaving the reaction vessel.

Examples of suitable starting materials for the reaction according to the invention are the monoesters of 1,2-propylene glycol with a carboxylic acid of 2 to 4 carbon atoms, especially with propionic acid and, preferably, acetic acid. Accordingly, the preferred starting material is 1,2- or 2,1-hydroxyacetoxypropane. These compounds are advantageously obtained by acetoxylation of propylene. This is described in detail in, for example, German Laid-Open Applications DOS Nos. 2,620,444, 2,636,669 and 2,636,670, French Pat. Nos. 1,421,288 and 1,419,966 and U.S. Pat. Nos. 3,542,857 and 3,262,969. As a rule, mixtures of 1,2-diacetoxypropane and 1,2-monoacetoxyhydroxypropanes are obtained.

The resulting mixtures can be subjected, as obtained, to the deacetoxylation according to the invention, but if water, or a compound which gives water under the reaction conditions, is absent, essentially only the monoacetate reacts.

To increase the conversion it is therefore advantageous either to introduce into the reaction the amount of water required to hydrolyze the diacetate to the monoacetate or to precede the reaction by a partial hydrolysis. In carrying out the latter, it is not detrimental that a proportion of the acetates is hydrolyzed to propylene glycol, provided the molar ratio of propylene glycol diacetate to propylene glycol does not become substantially less than 1. Accordingly, a mixture of propylene glycol diacetate and propylene glycol behaves as if the monoacetate were present, i.e. the conversion to the monoacetate takes place at high speed in the reaction mixture.

The stated mixtures are then brought into intimate contact, and mixed, with the solvent which is heated to the reaction temperature and contains the dissolved base, for a brief period, e.g. for from 0.1 second to 5 minutes, for example by adding the glycol acetates, batchwise or continuously, to the hot solution of the base, whilst stirring. Since the propylene oxide reaction product, and the by-products, which comprise allyl acetate, isopropyl acetate, propionaldehyde and possibly unconverted propylene glycol acetates, are vapors at the reaction temperature, they are evolved and can be trapped by condensing them and be separated by conventional methods. Whilst the resulting propylene oxide is advantageously subjected to a fine purification, the unconverted propylene glycol acetates and propylene glycol are recycled to the reaction.

According to another embodiment of the process, the mixture of the propylene glycol acetates can be brought into contact with the solution of the base, which has been heated to the reaction temperature, in counter-current or co-current in a tubular reactor, for example a packed column or a tray column, and the vapor products can be taken off.

A further possible method of bringing the components into intimate contact is to inject one component, for example the ester mixture, at high speed through the inner gap of a nozzle which consists of two coaxial tubes, into the high-boiling solvent containing the base, and to add some of the solvent through the annular gap to achieve thorough mixing.

The reaction is as a rule carried out at from 160° to 380° C., preferably from 190° to 350° C. It can also be carried out below and above these temperature limits. However, this does not have any advantages, since at low temperatures the conversion is inadequate whilst at higher temperatures the amount of by-products increases. The mixture of the propylene glycol acetates may be added without preheating or after preheating to, for example, 300° C., in the undiluted state or in solution in, for example, the solvent which is required for the reaction and acts as a heat transfer medium.

The reaction according to the invention is advantageously carried out under atmospheric pressure. However, with lower-boiling solvents it can in principle also be carried out under superatmospheric pressure though, due to the need to continuously let down the mixture in order to isolate the reaction products, this is more expensive and offers no particular advantage. Furthermore it is possible to lower the partial pressure of the vaporous reactants and products by at the same time passing an inert gas, e.g. nitrogen, through the reaction vessel. The reaction can also be guided in the desired direction by working under reduced pressure.

The solvents used for the deacyloxylation according to the invention must be inert under the reaction conditions, should boil above the reaction temperature, and must be sufficiently good solvents for all the reactants. This means that in the preferred method of working at atmospheric pressure, the solvent should have a boiling point of above 160° C. Further, it should not contain any functional groups which might react with a reaction product, e.g. with propylene oxide or acetic acid.

Accordingly, suitable high-boiling solvents are fairly high molecular weight aliphatic, cycloaliphatic, araliphatic or aromatic non-polar compounds or, preferably, high-boiling polar compounds, above all oxygen-containing and/or nitrogen-containing compounds in which the oxygen and nitrogen atoms are completely substituted.

Specific examples of suitable solvents are a mixture of isomeric triaryldimethanes, dimethyldiphenyl dioxide, 3-methyl-1-phenylindan, N-cyclohexylpyrrolidone, pentaethylene glycol methyl isopropyl diether, alkyltetrahydrothiophene-1,1-dioxide (where alkyl is, for example, methyl) and, preferably, tetrahydrothiophene-1,1-dioxide.

Suitable catalysts are any strong bases or salts of such bases with weak inorganic acids, especially with carbonic acid, or salts of the bases with fatty acids, e.g. the acids, such as acetic acid, formed during the reaction, provided the solubility of the catalyst in the solvent at the reaction temperature is sufficient, i.e. at least 1 g/l.

The bases may be organic or, preferably, inorganic compounds and should be so strongly basic that their 0.1-molar aqueous solution has a pH of at least 8, e.g. from 8 to 13.

Accordingly, alkali metal carbonates, alkali metal phosphates or alkali metal carboxylates, especially potassium acetate and preferably potassium carbonate, may be used. Sodium salts are equally suitable. The lithium compounds are also good catalysts. The concentration of the base in the organic solvent is as a rule from 0.1 to 12, preferably from 1 to 10, percent by weight based on the solvent.

Though it is advantageous to dissolve the base in the hot solvent which serves as the heat transfer medium and with which the glycol acetates are brought into contact, it is in principle also possible to add part or all of the base to the propylene glycol acetate, which may or may not be dissolved in a solvent of the above type, before the propylene glycol acetate is heated. However, this may result in an accumulation of the base in the solvent and may necessitate working up the latter.

On the other hand, such working up is in any case advisable after a lengthy period of operation, since experience has shown that after some time the by-products, formed in small amounts, which boil above the reaction temperature accumulate. This working up is advantageously effected by distillation, which may or may not be carried out under reduced pressure; the solvent purified in this way is then recycled to the deacyloxylation stage.

Specifically, the manufacture of propylene oxide by the process of the invention is advantageously carried out as follows; use of the acetate being described by way of example:

1. In the acetoxylation stage I, propylene is acetoxylated by conventional methods, for example by the process described in German Laid-Open Application DOS No. 2,620,444. A mixture of propylene glycol acetates predominantly consisting of the diacetate is obtained.

2. Since, as mentioned above, essentially only the monoacetates are deacetylated, it is necessary either to precede the reaction by appropriate hydrolysis of the propylene glycol diacetates or to introduce the required amount of water directly into the reaction. A combination of both measures is also feasible.

(a) According to the preferred embodiment, the mixture of propylene glycol monoacetate and propylene glycol diacetate obtained by acetoxylation is sprayed into the reaction zone together with about an equimolar amount, based on the amount of propylene glycol diacetate, of water; hydrolysis of the propylene glycol diacetate to propylene glycol monoacetate takes place in the reaction zone simultaneously with the deacetylation reaction.

The amount of water can also be less than the equimolar amount. Equally, a slight excess, for example 20% above the equimolar amount, can be used, but this reduces the yield since, unless corresponding amounts of propylene glycol diacetate are present, propylene glycol is not converted to propylene oxide.

(b) According to another embodiment, a partial hydrolysis of the acetoxylation mixture obtained as described under 1. is first carried out. This produces a mixture of propylene glycol monoacetates, propylene glycol diacetate and propylene glycol. This hydrolysis is advantageously taken no further than the production of an amount of propylene glycol equimolar to the non-hydrolyzed propylene glycol diacetate.

For this purpose, the mixture containing predominantly propylene glycol diacetate is hydrolyzed with from 50 to 200, preferably from 80 to 120, mole percent of water in the presence of a catalyst, e.g. sulfuric acid, or preferably in the presence of an organic cation exchanger containing sulfonic acid groups, at from 50° to 150° C., to give a mixture of propylene glycol diacetate, propylene glycol monoacetates and propylene glycol. Examples of organic cation exchangers containing sulfonic acid groups are sulfonated styrene/divinylbenzene copolymer resins, other sulfonated crosslinked styrene polymers and phenol/formaldehyde or benzene/formaldehyde resins containing sulfonic acid groups. The use of sulfonated styrene/divinylbenzene copolymer exchangers is preferred. The exchangers are employed in the acid form, not as salts. The particle size of the catalyst is from 10 to 200, preferably from 10 to 180, especially from 20 to 90, micrometers. Examples of suitable exchanger resins are those marketed under the name ®LEWASORB A-10. However it is also possible to use other commercial resins, e.g. ®AMBERLITE IR-120, ®DOWEX 50, ®LEWATIT S-100, ®NALCITE HCR, ®PERMUTIT RS and ®WOFATIT KPS-200 after milling them to the desired particle size.

As a rule, exchangers of normal coarse-grained consistency are employed, so that the reaction may be carried out either in suspension or in a fixed bed. Where a fixed catalyst is used it is necessary to ensure that the water required for hydrolysis is not withdrawn from the hydrolysis reaction by phase separation. Compared to mineral acids or carboxylic acids (e.g. acetic acid) as catalysts, cation exchangers offer substantial advantages, since they catalyst the hydrolysis at a high speed at substantially lower temperatures, especially below 100° C., and/or they can be separated off in a simple manner and hence do not cause the formation of by-products during hydrolysis and in the subsequent course of the process. Furthermore, this method permits reaction at atmospheric pressure or only slightly elevated pressure.

Any unreacted water, and the acetic acid formed, are isolated from the reaction mixture, for example by distillation, after filtering off the ion exchanger, and the acetic acid is returned to the acetoxylation stage.

3. To eliminate the carboxylic acid in the decarboxylation stage (III), the mixture of propylene glycol acetates, which may or may not be diluted with from 5 to 50% by weight of the high-boiling solvent, is added, with rapid mixing, to a solution, at from 160° to 380° C., preferably from 190° to 350° C., of the base in the high-boiling solvent which serves as the heat transfer medium, the addition taking place at the rate at which the reaction products are evolved from the reaction mixture, so that a mean residence time or reaction time of the propylene glycol acetates of from about 0.1 sec. to 5 minutes results. This corresponds, as a rule, to a rate of from 0.1 to 1 kg of monoacetate per kg of solvent per hour.

The products formed in the reaction, which, because of the high reaction temperature, are in the form of vapors, are condensed and/or are directly separated by distillation in the conventional manner, and unconverted acetates and propylene glycol are recycled to the reaction zone. The acetic acid formed is recycled to the acetoxylation stage I.

Further by-products formed are small amounts of propionaldehyde, acetone, i-propyl acetate, i-propanol, allyl acetate and allyl alcohol, which can be obtained in a pure form.

The propylene oxide obtained by distillation may or may not be subjected to conventional fine purification, and is used as a starting material for plastics, detergents, hydraulic fluids and deicing agents.

The deacetylation is a highly endothermic reaction so that large amounts of heat must be continuously supplied to the reaction medium. This is advantageously achieved by branching off part of the reaction medium, bringing it to a temperature which is up to 50° C. above the reaction temperature, and recycling it to the reaction zone.

In the Examples which follow, parts are by weight; parts by volume bear the same relation to parts by weight as that of the liter to the kilogram.

EXAMPLE 1

100 parts of tetrahydrothiophene-1,1-dioxide and 5.0 parts of potassium carbonate are introduced into a stirred vessel provided with a blade stirrer, internal thermometer and dip leg. 0.5 part by volume/min. of a propanediol diacetate/monoacetate mixture (in the molar ratio of 1:3) are pumped through the dip leg into the solution at 270° C., whilst stirring. The vapor evolved is condensed out in a cold trap (in order to determine the yield) and is examined by gas chromatography. In a 2 hour experiment, 60.0 parts of mixture (29.8% by weight of diacetate; 66.7% of monoacetates and 4.2% of diol) are employed; 68.3 parts of reaction product are obtained in the cold trap (7.7% of diol; 33.7% of monoacetate and 30.6% of diacetate). Accordingly, the conversion of monoacetate is calculated to be 42.5%. Using the definition that the selectivity (mole%) is $$\frac{\text{moles of PO}}{\Sigma \text{ moles of PO} + \text{propionaldehyde} + \text{acetone} + \text{i-propyl acetate} + \text{i-propanol} + \text{ally acetate} + \text{allyl alcohol}}$$

the selectivity is found to be 81.7%.

EXAMPLE 2

The procedure described in Example 1 is followed, but in addition 80 parts by volume of $N_2$/h are passed into the mixture. After 2 hours, 9.0 parts of tetrahydrothiphene-1,1-dioxide and catalyst remain in the stirred vessel; the cold trap contains 130.5 parts. The conversion is found to be 67.9% and the selectivity 80.0%.

EXAMPLES 3 TO 7

The procedure described in Example 1 or 2 is followed and the catalysts, temperatures and ratios shown in the Table which follows are employed; the selectivities achieved, as shown in the Table, are similar.

TABLE

| Example | Solvent (g) | Solvent (type) | Catalyst (g) | Catalyst (type) | g/h | Feed of acetates Composition (% by weight) HOAc | PDDA | PDMA | PD | Temperature of experiment (°C.) | Duration of experiment (h) | Conversion (mole %) | Selectivity (mole %) |
|---|---|---|---|---|---|---|---|---|---|---|---|---|---|
| 3 | 100 | tetrahydro-thiophene-1,1-dioxide | 5 | $K_2CO_3$ | 30 | 2.3 | 29.8 | 66.7 | 4.2 | 270–280 | 2 | 57.4 | 80.4 |
| 4 | 100 | " | 5 | KOAc | 30 | 2.3 | 29.8 | 66.7 | 4.2 | 250–270 | 2 | 47.5 | 74.3 |
| 5 | 100 | mixture of isomeric triaryl-dimethanes | 5 | $K_2CO_3$ | 30 | 2.3 | 29.8 | 66.7 | 4.2 | 300 | 2 | 43.6 | 76.3 |
| 6 | 100 | tetrahydro-thiophene-1,1-dioxide | 5 | $K_2CO_3$ | 30 | 0.02 | 62.5 (+ 80 l/h (S.T.P.) of $N_2$) | 39.7 | 0.08 | 240 | 2 | 55.5 | 76.6 |
| 7 | 100 | tetrahydro-thiophene- | 5 | $K_2CO_3$ | 30 | — | 67.8 | — | 32.2 | 250–260 | 2 | 72.3+ | 78.7 |

TABLE-continued

| Example | Solvent (g) | Solvent (type) | Catalyst (g) | Catalyst (type) | g/h | Feed of acetates Composition (% by weight) HOAc | PDDA | PDMA | PD | Temperature of experiment (°C.) | Duration of experiment (h) | Conversion (mole %) | Selectivity (mole %) |
|---|---|---|---|---|---|---|---|---|---|---|---|---|---|
| | | 1,1-dioxide | | | | | | | | | | | 83.7++) |

+based on PDDA
++based on PD
In the Table the abbreviations denote the following: HOAc = acetic acid; PDDA = 1,2-propanediol diacetate; PDMA = 1,2-propanediol monoacetate; PD = 1,2-propanediol

Propylene oxide purification

The product stream obtained as described in Examples 1 to 7 is fed to a column (for example inlet pressure 1 bar; top temperature 32°–35° C.; bottom temperature 135° C.; reflux ratio 30; 50 plates). Propylene oxide, propionaldehyde and acetone are obtained as the top product.

To isolate pure propylene oxide, a second distillation is carried out (for example inlet pressure 1 bar; top temperature 30° C.; reflux ratio 8; 85 plates) and pure propylene oxide is obtained as the top product.

EXAMPLE 8

100 parts of n-nonadecane and 5 parts of potassium carbonate are introduced into the apparatus described in Example 1. 60 parts of a diacetate/monoacetate mixture having the composition specified in Example 6 are supplied at a reaction temperature of 250° to 260° C. over a period of 2 hours. The conversion is found to be 24.3% and the selectivity 93.7%.

EXAMPLE 9

The procedure of Example 8 is followed, starting with a mixture of 90 parts of tetrahydrothiophene-1,1-dioxide and 10 parts of n-nonadecane. The conversion is 15.0% and the propylene oxide selectivity 95.5%.

EXAMPLE 10

The reaction is carried out using an apparatus of the type shown in FIG. 1, comprising a reactor 1, thermometer 2, separator 3, and cold traps 4 and 5.

A mixture of diacetate, monoacetates and diol is pumped into the system at 6 under atmospheric pressure. Phase separation between the solvent and the reactants takes place at the tube outlet, the gas phase being condensed and analyzed. Using the parameters set forth below the results are as follows:

| Feed Composition (% by weight) | g/h | Solvent | Temperature (°C.) | Duration of experiment | Result | |
|---|---|---|---|---|---|---|
| propanediol diacetate | 30 | tetrahydro-thiophene-1,1-dioxide | 260–270 | 2.2 | 9.5% propylene oxide in off-gas | selectivity |
| propanediol | | | | | 2.0% propylene oxide in condensate | 93% |

EXAMPLE 11 (FIG. 2)

A glass reaction tube 21 (length 20 cm, I.D. 35 mm) is fitted at its upper end with a conical ejector 22 (dia. 1.2 mm, 90° cone, as supplied by Messrs. Lechner). A heated gas-fluid separator 23 is provided at the lower end of the reactor. All fluid lines have electric heaters would around them. 2,150 g of tetrahydrothiophene-1,1-dioxide and 1% by weight of potassium acetate are introduced and the liquid is pumped through the nozzle at the rate of approx. 200 ml/min. A vapor mixture comprising propanediol di- and monoacetates and diol (300 g/h; 60.9 wt% diacetate; 20.1 wt% 1-monoacetate; 10.9 wt% 2-monoacetate; 7.7 wt% diol) is combined with the liquid jet (nozzle temperature approx. 280° to 285° C.). The off-gas has the following composition: 64.5 mole% propylene oxide, 22.4 mole% propionaldehyde, 6.9 mole% acetate. The $C_3H_6O$ isomer selectivity is 93.4%. After 10 hours of operation, the results are essentially unchanged.

We claim:

1. A process for the manufacture of propylene oxide by eliminating carboxylic acid from an ester of 1,2-propylene glycol in the presence of a base which comprises: heating a homogeneous solution of a monoester of 1,2-propylene glycol and a low-molecular weight carboxylic acid, or a homogeneous solution of a mixture of a propylene glycol diester with water or with propylene glycol alone or together with said monoester at temperatures of from 160°. to 380° C., in an organic solvent which boils above the reaction temperature at the prevailing pressure and selected from the group consisting of dimethyldiphenyl dioxide, 3-methyl-1-phenylindan, N-cyclohexylpyrrolidone, pentaethylene glycol methyl isopropyl diether, alkyltetrahydrothiophene-1,1-dioxide tetrahydrothiophene-1,1-dioxide and a mixture of isomeric triaryldimethanes, in the presence of a dissolved base or a basic-reacting salt of said base, and isolating propylene oxide from the vapor evolved.

2. A process as set forth in claim 1, wherein one or both 1,2-propylene glycol monoacetates are used.

3. A process as set forth in claim 1, wherein one or both 1,2-propylene glycol monoacetates are used mixed with 1,2-propylene glycol diacetate and propylene glycol.

4. A process as set forth in claim 1, wherein an alkali metal hydroxide, alkali metal carbonate or alkali metal acetate is used as the base.

5. A process as set forth in claim 1, wherein a mixture of one or both 1,2-propylene glycol monoacetates, propylene glycol diacetate and propylene glycol is brought into contact with a solution, at from 160° to 350° C., of a base or a salt of this base with a weak acid, especially with a low-molecular weight organic acid, and propylene oxide is isolated from the vapor evolved.

6. A process as set forth in claim 1, wherein propylene oxide, the unconverted 1,2-propylene glycol ester(s), propylene glycol and acetic acid are isolated from the reaction distillate, the unconverted ester(s) and the propylene glycol are recycled to the deacetylation and the recovered acetic acid is recycled to the acetoxylation of propylene to give the 1,2-propylene glycol esters.

* * * * *